United States Patent [19]

Upadhyay et al.

[11] Patent Number: 5,962,515
[45] Date of Patent: Oct. 5, 1999

[54] PROCESS FOR ISOLATION AND SYNTHESIS OF 1-(3,4 METHYLENEDIOXY-PHENYL)-1E-TETRADECENE AND ITS ANALOGUES AND THEIR ACTIVITIES AGAINST TUMORS AND INFECTIONS

[75] Inventors: Shakti N. Upadhyay; Ram A. Vishwakarma; Sabari Ghosal; Supriya Shukla; Chanda Bose; Anita Kamra, all of New Delhi, India

[73] Assignee: National Institute of Immunology, New Delhi, India

[21] Appl. No.: 08/865,152

[22] Filed: May 29, 1997

[51] Int. Cl.$^6$ .......................... A61K 31/36; A61K 31/70; C07D 317/48
[52] U.S. Cl. ............................ 514/464; 549/434; 514/27; 514/35
[58] Field of Search ............................... 549/434; 514/464

[56] References Cited

PUBLICATIONS

Likhitwitayawuid, K. Tetrahedron, vol. 43, No. 16, pp. 3689–3694, 1987.

*Primary Examiner*—Robert W. Ramsuer
*Assistant Examiner*—Taofiq A. Solola
*Attorney, Agent, or Firm*—Ladas & Parry

[57] ABSTRACT

Process for isolation of 1-(3,4-methylenedioxy-phenyl)-1E-tetradecene from Piper longum. Processes for synthesis of 1-(3,4-methylenedioxy-phenyl)-1E-tetradecene; its stereoisomers and analogues are disclosed. The compounds isolated and synthesized according to this invention have immunomodulatory properties and can be used to treat tumors and infections.

7 Claims, 5 Drawing Sheets

EFFECT OF 1-(3,4-METHYLENEDIOXY-PHENYL)-1E-TETRADECENE
ON THE PROLIFERATION OF P-815 TUMOR CELLS,
*IN VITRO* (THYMIDINE INCORPORATION ASSAY)

PROCESS FOR ISOLATION AND SYNTHESIS OF 1-(3,4 METHYLENEDIOXY-PHENYL)-1E-TETRADECENE AND ITS ANALOGUES AND THEIR ACTIVITIES AGAINST TUMORS AND INFECTIONS

BACKGROUND

Due to increasing incidence of cancer, in general, there is need to develop new therapeutic strategies. The current methods for treatment of tumors, besides radiation therapy and surgical interventions, include tumorcidal chemotherapeutic agents which act directly and are toxic to tumor cells. Such anti-tumor drugs, however, are generally associated with severe side effects as they often kill all normally dividing cells without discrimination. The present invention relates to an alternate strategy, referred to as immunomodulatory therapy, where instead of killing the tumor cell directly the drug is intended to act on the immune system and activate its effector mechanisms which in turn kills tumor cells. Immunomodulatory therapy thus relates to "educating" or "activating" the immune cells to react against and kill the tumor cells; the same strategy applies also to cells infected with parasites and/or viruses. The advantage is that the immune system is selective and it normally attacks only diseased/tumor cells, ignoring the normal healthy ones.

PRIOR ART

The idea of fighting cancer by unleashing the latent power of a patient's own immune system has been practiced since the early 20th century, when some physicians (William B. Coley) attempted this strategy by injecting patients with killed bacteria (Nauts H. C., The Bibliography of Reports Concerning the Experimental Clinical Use of Coley Toxins, Cancer Research Institute; New York, 1975). Recent advances in the field of immunology have revealed that tumor regression is carried out mainly by cytotoxic T lymphocytes (CTL) or activated macrophages. These cells recognize unique antigens displayed on the surface of tumor cells and become activated and kill the tumor cells. In addition, natural killer (NK) cells also play an important role for killing tumor cells.

A) Current Methods for Activation of Effector Mechanism of the Immune System

Ever since it has been demonstrated that human diseases can be treated by modulating the immune response, several immunomodulatory products have received clinical approval for therapeutic use in cancer and infections (reviewed by Hadden J. W., Trends in Pharmaceutical Sciences, 14: 169–174,1993). The list of clinically approved immunomodulators is given in the following table:

| AGENT | CHEMICAL NATURE | CLINICAL USE |
| --- | --- | --- |
| Microbially derived products: | | |
| BCG | Live mycobacteria | bladder cancer |
| Picibani | Extract: *Strp. pyrogenes* | gastric/other cancer |
| Krestin | fungal polysaccharide | gastric/other cancer |
| Lentinan | fungal polysaccharide | gastric/other cancer |
| Biostim | extract: *Klebsiella pneum* | chronic/recurrent infections |
| Broncho-Vaxom | extract of 8 bacteria | chronic/recurrent infections |
| Chemically defined products: | | |
| Romurtide | muramyl dipetide (MDP) | bone marrow recovery |
| Murabutide | MDP derivative | cancer/infection |
| Ubenimex (Bestatin) | dipeptide | cancer |
| Thymopentin TP-5 | pentapeptide | infection, cancer |
| Levamisole | phenylimidothiazole | cancer |
| Inosine pranobex | inosine-salt complex | infection |
| Poly AU | double-stranded poly-nucleotide of adenylic and uradylic acid | breast cancer |
| Ampligen | mismatched Poly 1C | HIV, cancer |

However, so far no plant derived immunomodulatory compound has reached the stage of clinical testing.

B) Piper Longum

The Indian medicinal plant Piper longum L, (family: piperaceae) grows and is cultivated in different parts of India and other south east Asian countries and root extracts and preparations are widely used in various Indian system of medicine including its high reputation in Ayurvedic medicine for treatment of diseases of the respiratory tract viz, cough, bronchitis, asthma etc; as counter-irritant and analgesic when applied locally for muscular pain and inflammation; as snuff in coma and drowsiness and internally as a carminative; as a sedative in insomnia and epilepsy; a general tonic and haematinic; as a cholagogue in obstruction of bile duct and gall bladder; as an emmenagogue and abortifacient; and for miscellaneous purposes as anthelmintic and in dysentery and leprosy (Atal and Ojha, Wealth of India, Vol. 8. Ph-Re. CSIR Publication, New Delhi). The detailed chemical investigations on the fruits of Piper longum and related species has led to identification of several pieridine alkaloids such as piperine, piplartine, piperlongumine, piperlonguminine, pipernonaline and piperundecalidine etc., a few hitherto unidentified steroids and some reducing sugars and their glycosides (Desai S. J. et al., Indian. J. Chem., 28B, 775, 1989, and the literature sited therein).

SUMMARY OF THE INVENTION

In our investigation on activity guided fractionation of this plant for compounds exhibiting immunolodulatory activity, we have isolated, among other compounds, a biologically active compound characterized as 1-(3,4-methylenedioxy-phenyl)-1E-tetradecene, as a new compound from the Piper longum species and developed a new high yielding chemical synthesis of 1-(3,4-methylenedioxy-phenyl)-1E-tetradecene and its stereoisomers and analogues having improved bioactivity, bioavailability and solubility. The structural formula of 1-(3,4-methylenedioxy-phenyl)-1E-tetradecene is:

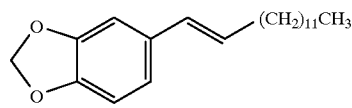

There is one report in literature (K. Likhitwitayawuid et. al., Tetrahedron, 1987, 43, 3689–3694) on isolation of similar compounds from Indonesian species Piper sarmentosum but no biological investigation for any kind of activity has been reported in the scientific and patent literature.

OBJECTIVES OF THE INVENTION

The main objectives of the present invention are 1) isolation and identification of immunomodulatory compound from Piper longum which enhances the effector mechanism of the immune system to react against tumors, 2) new synthetic process for generation of immunomodulatory compound from Piper longum, analogues and stereoisomers of these compounds, and 3) development of novel immunotherapeutic applications of these compounds against tumors and opportunistic infections such as bacterial and viral infections.

STATEMENT OF THE INVENTION

The present invention describes a new method of activating the immune system to react against tumors and infections by using a formulation containing 1-(3,4-methylenedioxy-phenyl)-1 E-tetradecene, isolated from the Piper longum preferably from the fruits of Piper longum. The present invention also describes a process of isolation of 1-(3,4-methylenedioxy-phenyl)-1E-tetradecene from Piper longum, a new process of synthesis of 1-(3,4-methylenedioxy-phenyl)-1E-tetradecene and also its synthetic analogues and stereoisomers with improved bioactivity and bioavailability. The extracted 1-(3,4-methylenedioxy-phenyl)-1E-tetradecene, chemically synthesized 1-(3,4-methylenedioxy-phenyl)-1E-tetradecene and its chemically synthesized analogues and stereoisomers can also be used to activate the immune system, treat tumors, treat bacterial and/or viral infections. These compounds can also be used to treat opportunistic infections such as mycobacteria causing tuberculosis in immunocompromised/immunodeficient mammals. A mammal could be immunocompromised or in an immunodeficient state due to tumor/radio or chemotherapy or due to a viral infection like HIV.

DETAILED DESCRIPTION OF THE INVENTION

Figure 1:
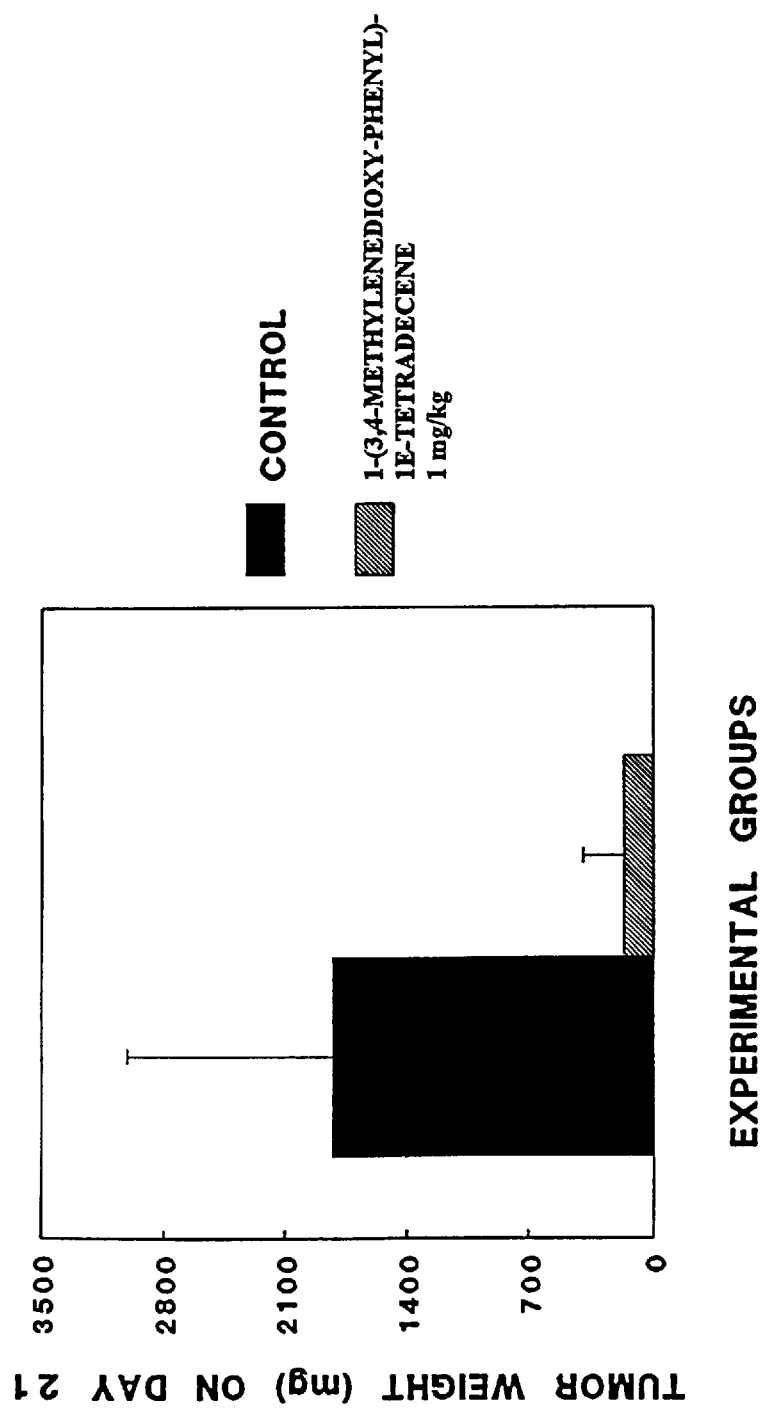
FIG. 1. Shows the effect of treatment with 1-(3,4-methylenedioxy-phenyl)-1E-tetradecene on P-815 tumor implant in DBA/2J mice.

The well characterized Piper longum fruits were dried, macerated and extracted by using a mixture of organic solvents and water. Other parts of Piper longum may be used. The extraction is by the solvent method. The dried and macerated parts can be extracted with alkyl monohydric alcohols having an alkyl chain length of $C_1$–$C_5$. Preferred alkyl monohydric alcohols are alcohols such as methanol, ethanol, propanol, isopropanol, butanol, etc. It is more preferred that methanol be used. The ratio of alcohol to water used varies from 5:5 to 9:1. In one embodiment of the invention, the ratio of methanol to water is 9:1. The time required for efficient extraction ranges from an hour to a few days depending on the amount of plant material to be extracted. 24 hour extraction was found to be optimum for efficient extraction. In one embodiment the extract was drained out after 24 hours and fresh solvent was added and the process was repeated several times. Additional solvent used in extraction is added to plant residue after removal of the earlier batch of solvent by decantation or filtration. At least 3 to 4 extractions are required for maximum extraction of the desired materials. Extraction is complete when the solvent becomes clear after repeated extractions. The extract is then concentrated below 50° C. Concentration can take place, for example, under reduced pressure in a rotary evaporator or by simple distillation in a glass assembly under reduced or atmospheric pressure. It is possible that the total weight of extract obtained after removal of solvent is approximately 10% (weight by weight) of the dried plant material used. The concentrated extract was solvent fractioned into hydrocarbon solvent, chlorinated hydrocarbon, ethyl acetate and water soluble fractions respectively. Examples of hydrocarbon solvents are petroleum fraction boiling at 40°–60° C. and 60–80° C. Other hydrocarbon solvents, like pentane, heptane etc., can also be used and hexane is also suitable. All the fractions were biologically tested for their ability to induce regression of P-8 15 solid tumor implant in DBA/2J mice and screening led to identification of active fraction. The biologically active fraction amongst all the fractions made was further purified by chromatographic methods on normal and reverse phase silica gel columns. The normal phase silica gel column chromatography of active fraction obtained by elution with various combinations of hydrocarbon and chlorinated hydrocarbons/alkyl ethers, for example with hexane, hexane-dichloromethane (9:1), hexane-dichloromethane (8:2), hexane-dichloromethane (7:3), hexane-dichloromethane (6:4), dichloromethane respectively. The fractions were concentrated, for example, under reduced pressure and homogeneity of the compounds determined by thin layer chromatography of fractions in different solvent systems. The repeated chromatography of biologically active fraction led to purification of four pure compounds which were separately screened for immunomodulatory activities. This led to identification of 1-(3,4-methylenedioxy-phenyl)-1E-tetradecene as the most active pure compound. Approximately 70 mg of 1-(3,4-methylenedioxy-phenyl)-1E-tetradecene can be isolated from one kilogram of dry weight of the plant material. The 1-(3,4-methylenedioxy-phenyl)-1E-tetradecene was recrystallized for example using ethanol-hexane (9:1). The mp is 34–36° C. The following is an example of isolation of this compound from Piper longum plant material, and this should not be construed to limit the scope of invention.

EXAMPLE 1

Isolation Method for 1-(3,4-methylenedioxy-phenyl)-1E-tetradecene

The Piper longum fruits were dried, powdered and extracted using a mixture of methanol: water (9:1) in a 10 liter capacity aspirator type extractor for 24 hours at room temperature. The extract was drained out after 24 hours and fresh solvent was added and the process was repeated five times. The extract was then concentrated below 50° C. under reduced pressure in a rotary evaporator. The concentrated extract (10% of total weight of extract was obtained on the basis of the weight of dried starting plant material) was solvent fractionated into hydrocarbon solvent, (petroleum fraction boiling at 40°–60° C. and 60°–80° C.), chlorinated hydrocarbons such as dichloromethane and chloroform, ethyl acetate and water soluble fractions respectively. All of the fractions were biologically tested for desired activity and this screening led to identification of active fraction. The biologically active fraction amongst all the fractions made was further purified by chromatographic methods on normal and reverse phase silica gel columns. The normal phase silica gel column chromatography of active fraction obtained by elution with various combinations of hydrocarbon and chlorinated hydrocarbons/alkyl ethers, for example with hexane, hexane-dichloromethane (9:1), hexane-dichloromethane (8:2), hexane-dichloromethane (7:3), hexane-dichloromethane (6:4), dichloromethane respectively. The fractions were concentrated under reduced pressure and homogeneity of the compounds determined by thin layer chromatography of fractions in different solvent systems. The repeated chromatography of biologically active fraction led to purification of four pure compounds which were separately screened for immunomodulatory activities. This led to identification of 1-(3,4-methylenedioxy-phenyl)-1E-tetradecene as the most active pure compound. 70 mg was isolated from one kilogram of dry weight of the plant material. The 1-(3,4-methylenedioxy-phenyl)-1E-tetradecene was recrystallized from ethanol-hexane (9.9:1), mp 34–36° C.

Structural Characterization 1-(3,4-methylenedioxy-phenyl)-1E-tetradecene is a low melting point solid, mp 34–36° C. with molecular formula $C_{21}H_{32}O_2$ as determined by mass spectrometric data (M+at m/z 316). The UV: 1 max (EtOH) 215, 220, 260 and 305 nm indicated the presence of an aromatic ring in the compound. The IR nmax cm-1 3019, 2937, 2953, 1550, 1540, 1200, 798 and 750 were the typical characteristic absorption bands of an aromatic moiety and it was clearly devoid of any free phenolic or carboxylic group. The 1H NMR (300 MHZ) spectrum of the 1-(3,4-methylenedioxy-phenyl)-1E-tetradecene exhibited typical characteristic peak of a methylenedioxy group in a benzene ring at d 5.89 (2H, s), two olefinic protons at d 6.45 and 6.01 (each 1H, d, J=16 Hz), three aromatic protons at d 6.858 (1H, d, J=1.6 Hz) and d 6.7 (2H, ill resolved multiplet). These chemical shifts altogether indicated that the compound contains one central benzene ring, two positions of which are substituted by methylenedioxy group and one of the two meta positions of this group is associated with an alkenyl side chain. The coupling constant value (J=16 Hz) confirmed the trans orientation of the olefinic double bond. In the upfield region peak at d 0.85 (3H, apparent t,) and d 2.125 (2H, q) showed a ethyl moiety attached with a saturated hydrocarbon long chain. A broad signal at d 1.21 (18H, m) and d 1.39 (2H, m) also supported the presence of the long hydrocarbon chain, but the actual length of the chain can only be confirmed by the mass spectral studies and chemical synthesis of compound. The EI mass spectrum of the compound showed the molecular ion peak at m/z 316. It also showed intense peaks at m/z 288, 161, 135, 131 and 103 which corresponds to the following ion fragments. The above mass spectral data clearly suggests the presence of a 3,4-methylenedioxy-phenyl moiety (C-7 unit) conjugated to an alkenyl side chain (C-14). The most convincing evidence in favor of the structure was obtained by 13C NMR studies and DEPT experiment of the compound. The three quaternary carbons at dc 148.0, 146.5, and 133.0 could be attributed to C-3, C-4, and C-1 respectively. Out of the five protonated carbon atoms three aromatic carbons appeared at dc 105.3, 108.2 and 120.1 corresponding to C-2, C-5 and C-6 and two olefinic carbons at d C 129.5 and 129.0 could be placed at C-1' and C-2' respectively. A sharp methylinic carbon at dc 101 confirmed the presence of methylenedioxy group and dc 23.5 ($CH_2$) and 14.5 ($CH_3$) suggested a terminal ethyl group in the side chain. The proton and carbon chemical shifts assignments were unambiguously confirmed by two-dimensional homo and heteronclear correlation NMR experiments. The spectral data discussed led to structure as 1-(3,4-methylenedioxy-phenyl)-1E-tetradecene.

Synthesis of 1-(3,4-methylenedioxy-phenyl)-1E-tetradecene and its Analogues and its Stereoisomers Keeping in mind the very limited amounts of 1-(3,4-methylenedioxy-phenyl)-1E-tetradecene that could be isolated from Piper longum and the pressing requirement for various in-vitro and in-vivo immunomodulatory antitumor and anti-infective activities, we decided to chemically synthesize 1-(3,4-methylenedioxy-phenyl)-1E-tetradecene and its analogues from commercially available and inexpensive starting materials. The other objective of developing synthetic methods was to enable us with the strategy for synthesis of non-natural cis-stereoisomer of 1-(3,4-methylenedioxy-phenyl)-1E-tetradecene and modified analogues with enhanced biological activity, solubility and bioavailability. Therefore a new high yielding Wittig olefination based chemical synthesis was successfully carried out using piperonal (heliotropin, 3,4-methylenedioxybenzaldehyde) and 1-tridecanol. This synthetic strategy is suitable for synthesis of 1-(3,4-methylenedioxy-phenyl)-1E-tetradecene and analogues having varying hydrocarbon chain length and structural and stereochemical modification at olefin and phenyl ring. The Osmium tetraoxide/Sodium chlorate and $OsO_4$/N-methylmorpholinoxide mediated cis-dihydroxylation of olefinic bond of 1-(3,4-methylenedioxy-phenyl)-1E-tetradecene led to synthesis of 1-(3,4-methylenedioxy-phenyl)-1,2-dihydroxy-tetradecane. In order to prepare water soluble analogues of 1-(3,4-methylenedioxy-phenyl)-1E-tetradecene, synthetic 1-(3,4-methylenedioxy-phenyl)-1,2-dihydroxy-tetradecane was monoglycosylated at benzylic hydroxyl position with various tetra-acetylglycosyl halides under Koeing-Knorr coupling conditions followed by deacetylation to provide water soluble glycosides of 1-(3,4-methylenedioxy-phenyl)-1E-tetradecene. This strategy can be used for preparation of various hexose and pentose O-glycosides. The following is an example to demonstrate in detail the experimental feasibility of the synthesis and this should not be construed to limit the scope of invention.

EXAMPLE 2

Example of Chemical Synthesis (i) Preparation of 1-bromotridecane: A solution of 1-tridecanol (8.80 g, 0.044 mole) in hydrobromic acid (48%, 14 g, bp 126° C.) and concentrated sulfuric acid (4.4 g, 2.4 ml) was heated to reflux for 5 hours at 110° C. The reaction mixture was cooled and diluted with ice cold water. The alkyl bromide layer was separated and washed with a small amount of conc. sulphuric acid and again with cold water. The oily layer was dried over anhydrous sodium carbonate and freshly fused calcium chloride. The product was distilled under high vacuum and the fraction distilling at 200° C. was collected. The desired 1-bromotridecane was obtained in 95% yield and was characterized by NMR and mass spectrometric techniques.

(ii) Preparation of tridecanyl-triphenylphosphonium bromide. The solution of tridecanyl bromide (2.63 g, 1 mmol), triphenylphosphine (2.63 g, 1 mmol) in benzonitrile (10 ml) was heated at 18000 for three hours. After completion of the reaction the excess of benzonitrile was removed by distillation under reduced pressure and to this was then added 10 ml of dry benzene and evaporated; this benzene azeotroping step was repeated three times to give pale yellow semi solid tridecanyl-triphenylphosphonium bromide in quantitative yield and this material was immediately used in the next step of the Wittig reaction.

(iii) Preparation of 1-(3,4-methylenedioxy-phenyl)-1E-tetradecene and 1-(3,4-methylenedioxy-phenyl)-1Z-tetradecene; The n-Butyl-lithium solution (0.0013 mole, 1 ml of 1.6 molar solution of n-BuLi in hexane) was added strictly under nitrogen atmosphere, to a suspension of tridecanyl-triphenylphosphonium bromide (525 mg, 0.001 mole) in dry benzene (2 ml) and the solution was stirred for two hours. Piperonal (heliotropin, 150 mg, 0.001 mole) dissolved in dry benzene (1 ml) was added by an air tight syringe and the reaction mixture was further stirred at room temperature for an additional 4 hours and after that it was diluted with petroleum-ether (40–60° C.). The supernatant was collected, washed with water and dried with anhydrous sodium sulfate and concentrated to give 80% yield of 70:30 trans-cis diastereoisomeric mixture of 1-(3,4-methylenedioxy-phenyl)-1E-tetradecene and 1-(3,4-methylenedioxy-phenyl)-1Z-tetradecene.

The structural formula of 1-(3,4-methylenedioxy-phenyl)-1Z-tetradecene is

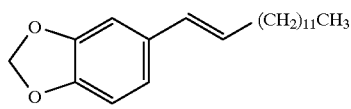

The isomers were separated by silica gel column chromatography and analytically pure samples were obtained by high performance liquid chromatography using cyclohexane-ethyl acetate eluant on a normal phase HPLC column. The identity of synthetic 1-(3,4-methylenedioxy-phenyl)-1E-tetradecene was confirmed by comparison of its spectroscopic data with that of natural product isolated from Piper longum as described previously.

(iv) Preparation of 1-(3,4-methylenedioxy-phenyl)-1,2-cis-dihydroxy-tetradecane: To a suspension of synthetic 1-(3,4-methylenedioxy-phenyl)-1E-tetradecene (500 mg) in methanol (10 ml) was added 1% aqueous solution of Osmium tetroxide (2 ml) and 30% solution of hydrogen peroxide (2 ml). The mixture was stirred for 48 hours under inert atmosphere until completion of dihydroxylation. The reaction mixture was concentrated under reduced pressure and extracted into ethyl acetate. The organic layer was dried with sodium sulfate and concentrated to give residue that was chromatographed on silica column to give pure 1-(3,4-methylenedioxy-phenyl)-1,2-cis-dihydroxy-tetradecane (400 mg).

The structural formula of 1-(3,4-methylenedioxy-phenyl)-1, 2-cis-dihydroxy-tetradecene is

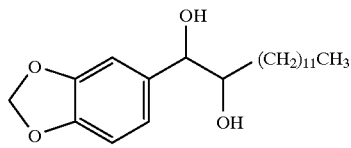

Formulation 1-(3,4-methylenedioxy-phenyl)-1E-tetradecene can be used alone or in combination with any other immunomodulator, anti-tumor and/or anti-biotic compound. The compound can also be combined with pharmaceutically accepted additives, diluents, carriers, and solvents. The compound can be administered orally in the form of a tablet, capsule or liquid etc., or injected i.p., i.m., s.c, or i.v. or can be applied topically in the form of a powder, cream, jelly or spray dosage. The active compound can be administered to obtain a dosage of 0.1 to 10 mg/kg body weight. The dosage may be given as a single dose per day or divided into multiple doses per day.

EXAMPLE 3

Examples of Therapeutic Applications

The present invention is illustrated by way of the following experimental studies and such experiments should not be construed as limiting the scope of the invention. P-815 tumor implant in DBA/2J mice was used as an animal model for this invention. P-815 tumor is known for its sensitivity to cytotoxic killing by activated lymphocytes and macrophages.

EXAMPLE 3A

Inbred DBA/2J mice were inoculated sub-cutaneously with P 815 tumor cells ($4 \times 10^6$ at a single site) on day 0 and animals were treated with 1-(3,4-methylenedioxy-phenyl)-1E-tetradecene, with a dose range of 0.1 to 10 mg/kg body weight (preferably 1 mg/kg body weight) starting day 1 post-tumor inoculation. Treatment in each group was given daily for 21 days and the tumor size was recorded at weekly intervals. The results showed that treatment with 1-(3,4-methylenedioxy-phenyl)-1E-tetradecene significantly arrested the tumor growth (FIG. 1).

EXAMPLE 3B

Figure 2:
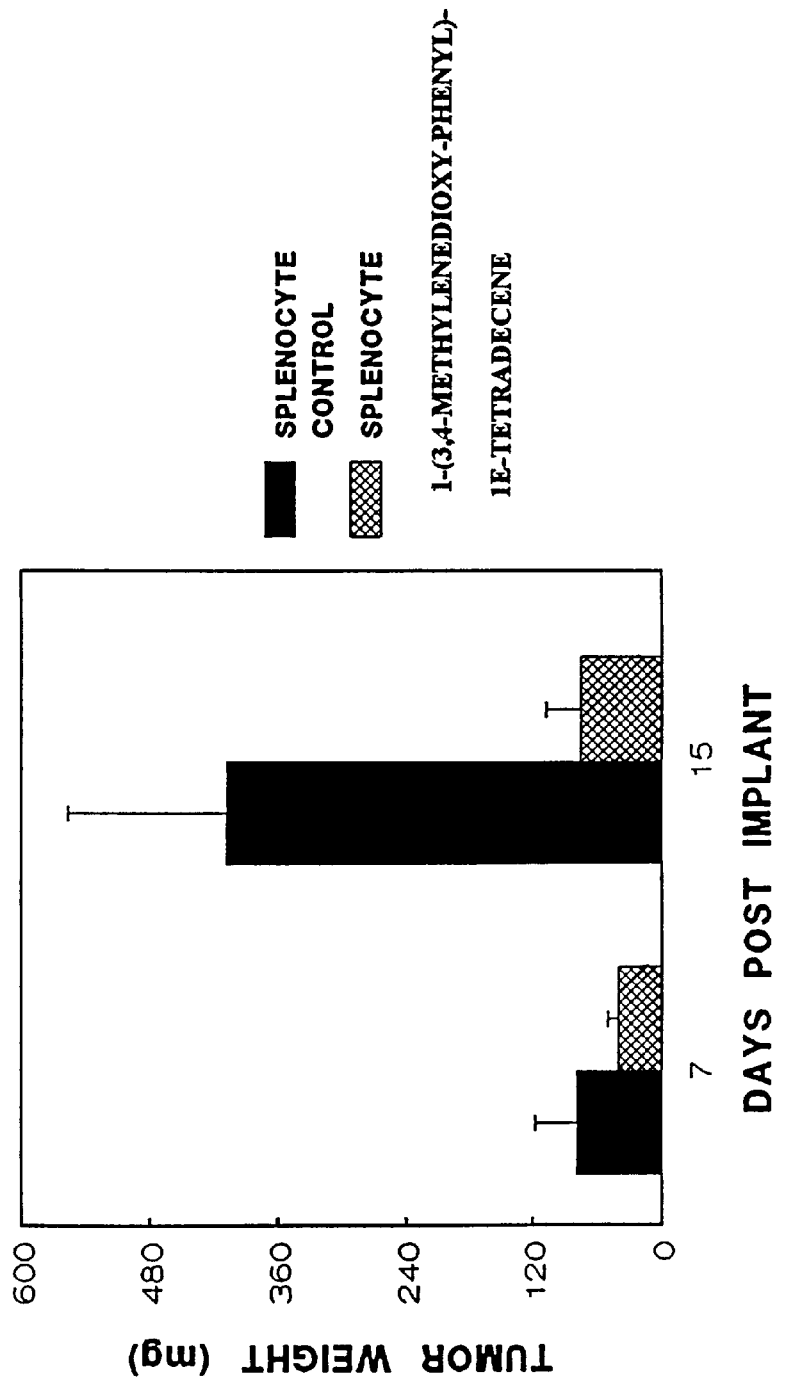
FIG. 2. Shows the effect of adoptive transfer of 1-(3,4-methylenedioxy-phenyl)-1E-tetradecene treated splenocytes on mice with tumors.

Inbred DBA/2J mice were treated with 1-(3,4-methylenedioxy-phenyl)-1E-tetradecene, at a dose of I mg/kg body weight for 7 days. On day 8, splenocytes were removed from these animals and were injected intravenously into DBA/2J mice inoculated sub-cutaneously with P-8 15 tumor cells. No treatment was given to tumor bearing mice. The results showed that adoptive transfer of splenocytes from 1-(3,4-methylenedioxy-phenyl)-1E-tetradecene treated mice to tumor-bearing mice caused significant reduction in tumor size, indicating that the anti-tumor effect of 1-(3,4-methylenedioxy-phenyl)-1E-tetradecene is mediated by the immunocompetent cells (FIG. 2).

EXAMPLE 3C

Figure 3:
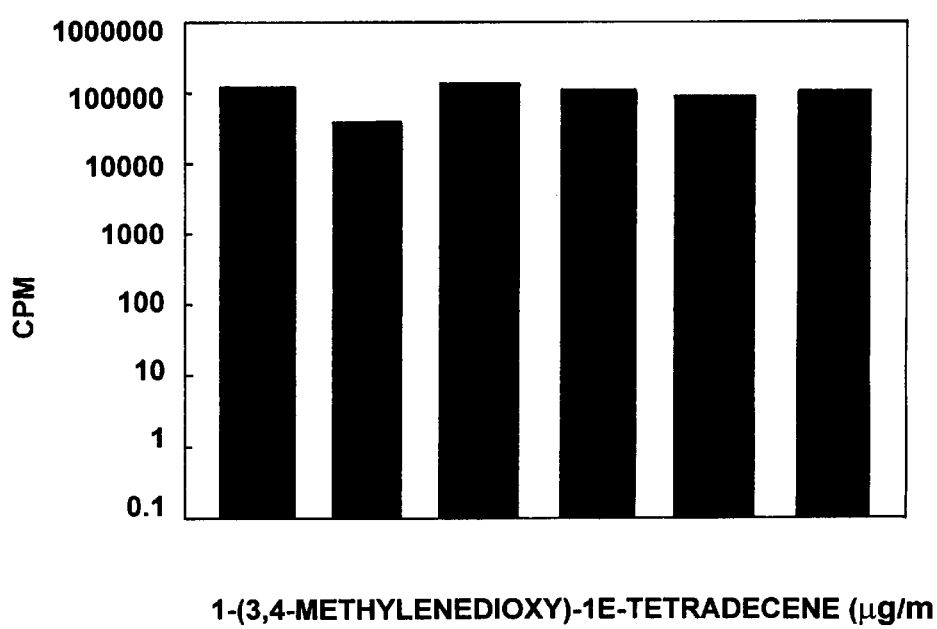
FIG. 3. Shows the effect of 1-(3,4-methylenedioxy-phenyl)-1E-tetradecene on the proliferation of P-815 tumor cells, in vitro (Thymidine Incorporation Assay).

P-815 tumor cells were cultured in vitro in the presence of various concentration of 1-(3,4-methylenedioxy-phenyl)-1E-tetradecene. After 48 hours, 3H-thymidine was added and cells were harvested after 6 hours. Incorporation of radio-labeled thymidine was counted using beta counter. CPM (counts per minute) indicated the cell division. Results showed that 1-(3,4-methylenedioxy-phenyl)-1E-tetradecene did not affect the viability and proliferation of P-815 tumor cells (FIG. 3).

EXAMPLE 3D

Figure 4:
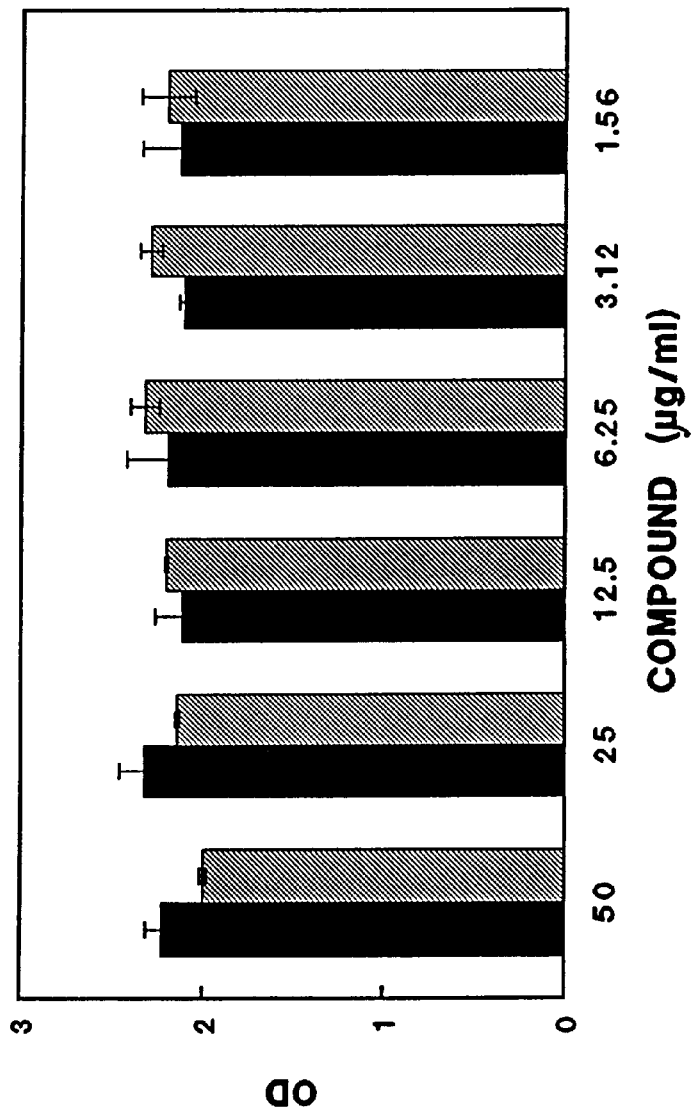
FIG. 4. Shows the effect of 1-(3,4-methylenedioxy-phenyl)-1E-tetradecene on viability of P-815 tumor cells (MTT Assay).

P-815 tumor cells were cultured in vitro in the presence of various concentration of 1-(3,4-methylenedioxy-phenyl)-1E-tetradecene. After 48 hours, MTT assay was carried out and the OD was recorded. Results showed that 1-(3,4-methylenedioxy-phenyl)-1E-tetradecene, even at a dose of 50 ug/ml did not significantly affect the viability and proliferation of P-815 tumor cells (FIG. 4), where as the effective dose of this compound in animals is only 20 ug/mice (1 mg/kg for 20 g body weight of mice) per day.

EXAMPLE 3E

Figure 5:
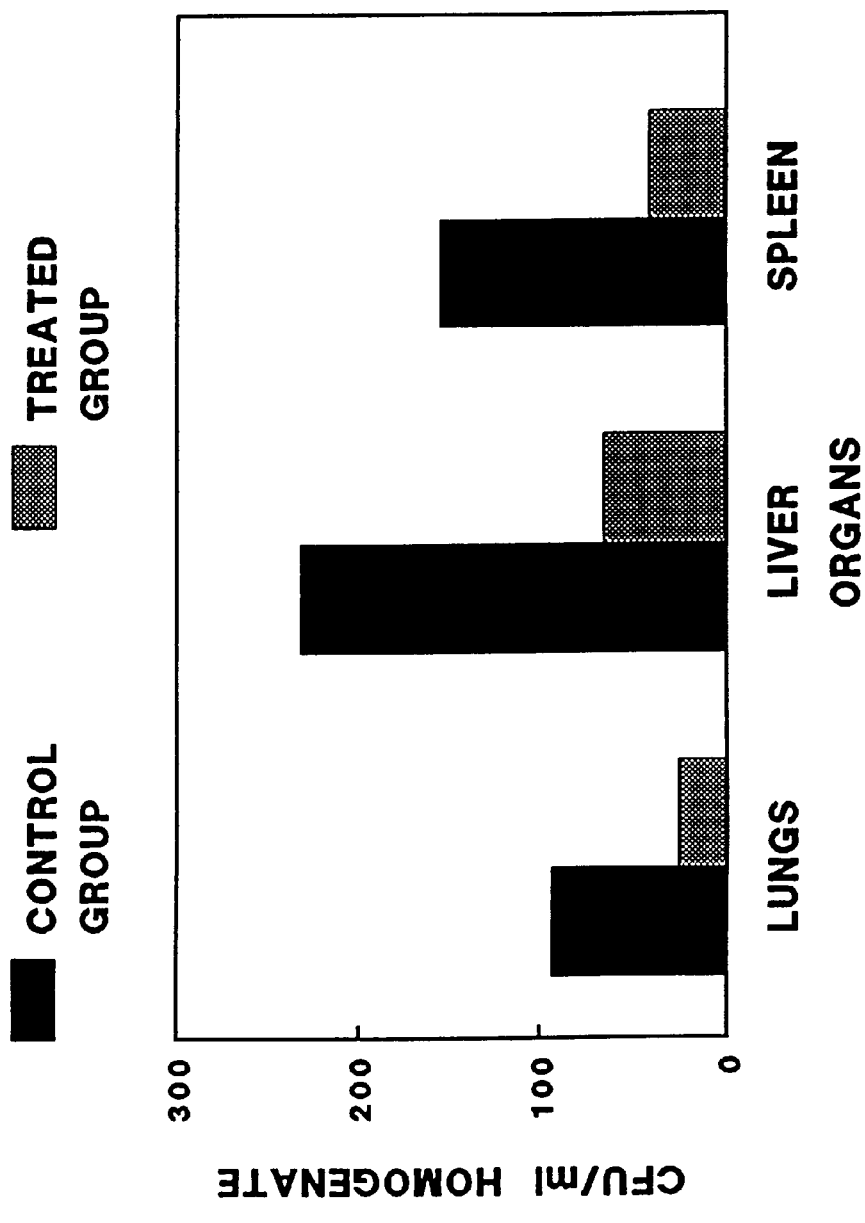
FIG. 5. Shows the effect of 1-(3,4-methylenedioxy-phenyl)-1E-tetradecene on mycobacterial infection in tumor bearing mice.

Inbred DBA/2J mice were inoculated sub-cutaneously with P-815 tumor cells ($4\times10^6$ at a single site) on day-0 and on day 7 these animals were infected with mycobacterium smegmetis ($10^6$) i.v injection. Starting day 8, the experimental group received daily treatment with 1-(3,4-methylenedioxy-phenyl)-1E-tetradecene, with a dose range of 0.1 to 10 mg/kg body weight (preferably 1 mg /kg body weight); untreated group (tumor bearing and mycobacteria infected) was maintained as control. All animals were sacrificed on day 15, and liver was removed, homogenized and plated on agar plates for mycobacterial colony counts. The results showed that treatment with 1-(3,4-methylenedioxy-phenyl)-1E-tetradecene significantly reduced the mycobacterial infection in tumor-bearing immunocomprised mice. (FIG. 5).

The stereoisomers and analogues have been tested in animal models and the results are comparable to the results obtained using 1-(3,4-methylenedioxy-phenyl)-1E-tetradecene.

We claim:

1. A pharmaceutical composition comprising 1-(3,4-methylenedioxy-phenyl)1E-tetradecene, its stereoisomers, hexose glycoside of 1-(3,4-methlenedioxy-phenyl)-1E-tetradecene,or pentose O-glycoside of 1-(3,4-methylenedioxy-phenyl)-1E-tetradecene and an immunodulator, anti-tumor or anti-biotic compound and a pharmacologically acceptable carrier, diluent or solvent.

2. A method of activating the immune system comprising administering a composition comprising 1-(3,4-methylenedioxy-phenyl)-1E-tetradecene, its stereoisomers, hexose glycoside of 1-(3,4-methylenedioxy-phenyl)-1E-tetradecene or pentose O-glycoside of 1-(3,4-methylenedioxy-phenyl)-1E-tetradecene and a pharmacologically acceptable carrier, diluent or solvent to a mammal.

3. The method of claim 2 wherein the composition is administered orally, topically, intraperitoneally, intravenously, intramuscularly, or subcutaneously.

4. A method for treating a tumor comprising administering to a mammal in need of such treatment an amount of 1-(3,4-methylenedioxy-phenyl)-1E-tetradecene, its stereoisomers, hexose glycoside of 1-(3,4-methylenedioxy-phenyl)-1E-tetradecene or pentose O-glycoside of 1-(3,4-methylenedioxy-phenyl)-1E-tetradecene effective to activate the immune system of the mammal.

5. A method for treating viral infection comprising administering an effective amount of 1-(3,4-methylenedioxy-phenyl)-1E-tetradecene, its stereoisomers, hexose glycoside of 1-(3,4-methylenedioxy-phenyl)-1E-tetradecene or pentose O-glycoside of 1-(3,4-methylenedioxy-phenyl)-1E-tetradecene to a mammal having the viral infection.

6. A method for treating a bacterial infection comprising administering an effective amount of 1-(3,4-methylenedioxy-phenyl)-1E-tetradecene, its stereoisomers, hexose glycoside of 1-(3,4-methylenedioxy-phenyl)-1 E-tetradecene or pentose O-glycoside-of 1-(3,4-methylenedioxy-phenyl)-1E-tetradecene to a mammal having the bacterial infection.

7. A method for treating an opportunistic infection in an immunocomprised or immunodeficient mammal comprising administering an effective amount of 1-(3,4-methylenedioxy-phenyl)-1E-tetradecene, its stereoisomers, hexose glycoside of 1-(3,4-methylenedioxy-phenyl)-1E-tetradecene or pentose O-glycoside of 1-(3,4-methylenedioxy-phenyl)-1E-tetradecene to said mammal.

* * * * *